(12) United States Patent
Corin et al.

(10) Patent No.: US 6,184,228 B1
(45) Date of Patent: Feb. 6, 2001

(54) ANTI-SICKLING AGENTS: SELECTION METHODS AND EFFECTIVE COMPOUNDS

(75) Inventors: Alan F. Corin, Sudbury; Andrew A. Pakula, Lexington; Julianne Bryan, Medford, all of MA (US)

(73) Assignee: ANADYS Pharmaceuticals, Inc., Waltham, MA (US)

( * ) Notice: Under 35 U.S.C. 154(b), the term of this patent shall be extended for 0 days.

(21) Appl. No.: 09/318,162

(22) Filed: May 25, 1999

(51) Int. Cl.$^7$ .......................... A61K 31/44; A61K 31/47; C07D 221/18; C07D 217/00; C07D 217/22

(52) U.S. Cl. .......................... 514/280; 514/284; 514/307; 514/291; 514/358; 546/71; 546/139; 546/143; 546/90; 546/347; 546/146; 546/48

(58) Field of Search ...................................... 514/284, 291, 514/358, 280; 546/71, 73, 139, 307, 143, 90, 347, 146, 48

(56) References Cited

U.S. PATENT DOCUMENTS

| | | | |
|---|---|---|---|
| 3,920,665 | * 11/1975 | Shimada et al. | ...................... 260/286 |
| 5,585,277 | 12/1996 | Bowie et al. | . |
| 5,679,582 | 10/1997 | Bowie et al. | . |

OTHER PUBLICATIONS

Bradsher, et. al., Aromatic Cyclodehdration NLVL Synthesis of Tetrahydropalmatine and Its Analogs, J. Org. Chem., vol. 26, pp. 2231–2234, 1961.*

Harrington, et. al., Ligand kinetics of hemoglobin S containing erythrocytes, Proc. Natl. Acad. Sci. USA, pp. 203–206, 1977.*

* cited by examiner

Primary Examiner—John Kight
Assistant Examiner—Binta Robinson
(74) Attorney, Agent, or Firm—Mark H. Weygandt; Timothy J. Martin; Michael R. Henson (57) ABSTRACT

The present invention is directed to a method for selecting compounds for use in treating sickle cell disease in a patient. The method comprises the steps of selecting a first set of HbS ligands from a first group of chemical compounds, selecting from the first set of HbS ligands a seconds set that exhibit inhibition of HbS polymerization, and selecting from the second set a third set that display anti-sickling activity of red blood cells when in the presence thereof. The method may include the step of performing a methemoglobin S proteolysis assay measuring a percent protease protection for each compound. The method may additionally include the steps of measuring HbS aggregation, inhibition of protease, deoxy-HbS gelation inhibition activity, $O_2$ affinity of HbS, and cytotoxic effect to cell activity. The method may further include assessing red blood cell morphology, and eliminating compounds that contain moieties that bind to heme. The steps of the method may be repeated on analogs of compounds that are selected using one or more steps of the method. The present invention also includes a method of treating sickle cell disease in a patient, which comprises administering to the patient a pharmaceutical formulation including a selected concentration of an HbS ligand and a pharmaceutically acceptable carrier therefore. The HbS ligand, which may be an isoquinolium derivative, is one exhibiting inhibition of HbS polymerization and displaying anti-sickling activity of red blood cells when in the presence thereof.

28 Claims, 2 Drawing Sheets

ANTI-SICKLING AGENTS: SELECTION METHODS AND EFFECTIVE COMPOUNDS

FIELD OF THE INVENTION

The present invention is directed to the treatment of sickle cell disease. Specifically, the present invention is directed to methods for selecting compounds for use in treating sickle cell disease. In particular, the present invention is directed to an affinity-based screening approach to discovering new anti-sickling agents. In addition, the present invention is directed to pharmaceutical formulations including new anti-sickling agents for use in treating sickle cell disease. In particular, the anti-sickling agents of the present invention relate to quaternary ammonium salts, and more specifically, isoquinolium derivatives. The present invention is also directed to methods of treating sickle cell disease in a patient, including administering to a patient a pharmaceutical formulation including new anti-sickling agents.

BACKGROUND OF THE INVENTION

The molecular origins of sickle cell disease ("SCD") are rooted in the tetrameric, $\alpha_2\beta_2$, hemoglobin molecule, the blood's $O_2$ and $CO_2$ molecular transporter. Pauling et al, 110 Science 543–48 (1949). SCD is believed to be caused by a single point mutation in the gene coding for the $\beta$ polypeptide chain of hemoglobin A ("HbA"), resulting in an amino acid change from glutamic acid to valine at position 6. Individuals who are homozygous for the hemoglobin S ("HbS") allele suffer severe medical consequences. In contrast, individuals who are heterozygous are rarely affected. The medical consequences arise because the deoxygenated form of HbS ("deoxy-HbS") exhibits a dramatic reduction in solubility relative to the deoxygenated form of HbA ("deoxy-HbA"). Deoxy-HbS polymerizes into aggregating fibers, which form a viscous gel that distorts the normally biconcave disc shape of normal erythrocytes into a characteristic banana or "sickle" shape. Wellems et al., 135 J. Mol. Biol. 651–74 (1979). The sickled cells are more rigid and less deformable than normal erythrocytes, which causes hemolysis and microvascular occlusion and leads to numerous pathologies including painful crises, organ damage and a reduced life expectancy. Dean et al., 299 New Engl. J. Med. 752–63, 804–11, 863–70 (1978); Hebbel, 77 Blood 214–37 (1991).

The rate of deoxy HbS polymerization is highly dependent on the initial cellular concentration of HbS, such that small decreases in the concentration of HbS tetramers capable of polymerizing can dramatically slow the rate of deoxy-HbS polymerization. Hofrichter et al., 73 Proc. Nat. Acad Sci., U.S.A. 3035–39 (1976); Eaton et al., 70 Blood 1245–66 (1987); Hofrichter et al., 71 Proc. Nat. Acad Sci. U.S.A. 4864–68 (1974). It has been suggested that a 15-20% decrease in the HbS population participating in polymer formation may decrease the severity of the disease to that of the less severe S/$\beta^+$-thalasemia, and be of significant therapeutic value. Sunshine et al., 275 Nature 238–40 (1978). Various chemotherapeutic approaches have been based on this strategy.

The problem of finding potent noncovalent gelation inhibitors for possible development in the treatment of sickle cell disease has been evident for over a quarter of a century. Gorecki et al., 77 Proc. Nat. Acad. Sci., U.S.A. 181–85 (1980). The molecular target, HbS, is well known and in abundant supply. Nonetheless, there are no anti-sickling agents to date approved for clinical use. There are at least two compounds undergoing serious clinical evaluation as therapeutics for SCD: a surfactant, poloxamer 188, for reducing the stickiness of sickle cells, and hydroxyurea for enhancing the production of fetal Hb, an effective diluent and inhibitor of the polymerizable HbS. Adams-Graves et al., 90 Blood 2041–46 (1997); Bridges et al., 88 Blood 4701–10 (1996); Charache et al., 332 New Engl. J. Med. 1317–22 (1995); Platt, 74 J. Clin. Invest. 652–56 (1984).

An alternative therapeutic strategy involves the use of small organic ligands that bind to HbS and interfere with the polymerization reaction. One starting point in a search for such molecules has been the use of high resolution crystal structures of small molecule-hemoglobin complexes. In that approach, compounds that hinder HbS polymerization were designed, yielding a number of compounds that have clear activity in inhibiting HbS polymerization. Abraham et al., 25 J. Med. Chem. 1015–17 (1982). However, with the exception of a number of ethacrynic acid analogues, most would have to be administered at rather high (ca. 5 mM) concentrations to achieve a therapeutically significant effect. Abraham et al., 32 J. Med. Chem. 2460–67 (1989); Abraham et al., 27 J. Med. Chem. 967–78 (1984); Abraham et al., 27 J. Med. Chem. 1549–59 (1984); Fatope et al., 30 J. Med. Chem. 1973–77 (1987).

Small organic molecules have been used to bind to HbS noncovalently, thereby inhibiting the intermolecular interactions required for aggregation. Gorecki et al., 77 Proc. Nat. Acad. Sci., U.S.A. 181–85 (1980); Abraham et al., 27 J. Med. Chem. 967–78 (1984); Belie et al., 18 Biochemistry 4196–201 (1979); Elbaum et al., 71 Proc. Nat. Acad. Sci., U.S.A. 4718–22 (1974); Noguchi et al., 17 Biochemistry 5455–59 (1978); Ross et al., 77 Biochem. Biophys. Res. Comm. 1217–23 (1977). However, most compounds examined to date have shown limited potency in enhancing deoxy-HbS solubility. This modest success is the result, in part, of limitations in screening. Existing functional assays, like the $C_{sat}$ assay to determine HbS solubility, Mazhani et al., Hemoglobin, 129–136 (1984), are too cumbersome to permit extensive screening.

The development of new small molecule therapeutics typically begins with the identification of an active, or lead, compound that exhibits some of the properties required for safe and effective therapeutic intervention. Compounds with improved properties are subsequently derived through iterative cycles of analog preparation and testing. Lead compounds are often identified using high throughput screening (HTS), whereby large libraries containing 50,000 to 1,000,000 compounds are tested using relatively simple assays to measure inhibition of processes critical to the target indication. Typically this means using biochemical assays to measure the function of one or more macromolecular targets.

However, functional assays appropriate for HTS can be difficult to establish as they require that: the biochemical process is well understood; the molecular participants are identified and available, often in large quantities; and the technologies needed to measure the relevant biochemical events are compatible with HTS. Such assays may also oversimplify the targeted process by probing only one function of a multifunctional macromolecular target. Sometimes assays based on intact cells can be used, allowing many aspects of a process to be targeted simultaneously. However, such measurements often generate less reproducible data than high quality biochemical assays and only detect active compounds that readily enter the cells and remain stable to cellular metabolic processes. Very often interesting compounds are identified in cell-based assays, but further development is impeded by an inability to identify the specific molecular target.

Many of the difficulties associated with HTS based on complex biochemical or cell-based assays can be circumvented by using an affinity-based primary screen. This is a universal approach since all lead compounds share the common property that they must bind to their macromolecular targets. Screening by affinity identifies a small subset of ligands which can be subsequently tested for function using a variety of low throughput biochemical and cell-based assays. Complex functional assays, unsuitable for high throughput use, can be employed to identify active compounds among the members of the smaller, more manageable ligand library. All ligands from the original library should be identified. Therefore, when multiple biochemical activities of the target are known, all the activities of each ligand can be measured separately without the prohibitive effort that would be needed to screen the entire library using multiple functional assays. When cell-based assays are available, affinity prescreening allows high throughput discovery even for macromolecular targets whose biochemical activities are uncharacterized. In contrast to the case for cell-based primary screens, determination of the molecular target of active compounds identified through cell-based secondary assays of known ligands is usually unnecessary.

A variety of affinity screening approaches have been described, including several strategies involving solid phase display of synthetic compounds produced through combinatorial synthesis, bacteriophage and bacterial display of random peptide libraries, and in vitro selection of RNA and DNA ligands to target proteins. Terrett et al., 51 Tetrahedron 8135–73 (1995); Scott et al., 249 Science 386–90 (1990); Lu et al., 13 Bio/Technology 366–72 (1995); Tuerk, 67 Meth. Mol. Biol. 219–30 (1997). Each of these methods significantly limits the types of compounds that can be assayed. None are compatible with screening natural product extracts or the vast collections of individually synthesized small molecules that are the traditional sources of compound diversity employed in drug discovery. Since these methods involve separation steps to differentiate bound from unbound material, they are unable to detect the binding of ligands whose dissociation half lives are significantly shorter than the time of separation. Ligands with micromolar dissociation constants typically dissociate with half lives far shorter than one second; therefore, only very high affinity ligands can usually be detected.

High throughput binding assays that require no separation steps have generally been unavailable. Recently, methods have been described wherein mass spectroscopy is used to directly measure protein-ligand complexes. Loo, 16 Mass Spec. Rev. 1–23 (1997). However, because there can be large variations in the stability of complexes upon desolvation from solution to the gas phase of the mass spectrometer, the generality of this approach is uncertain.

Accordingly, it can be seen that there is a need for new methods for selecting new small molecule thereapeutics for use in the treatment of sickle cell disease. Further, it can be seen that there is a need for new compounds useful in pharmaceutical formulations for treating sickle cell disease.

SUMMARY OF THE INVENTION

It is an object of the present invention to provide a new and efficient method for selecting compounds for use in treating sickle cell disease.

It is a further object of the present invention to provide an efficient method for screening large commercial libraries of chemical compounds to discover new compounds for use in treating sickle cell disease.

Still a further object of the present invention is to provide a method of treating sickle cell disease in a patient.

An additional object of the present invention is to provide pharmaceutical formulations for use in treating sickle cell disease, which pharmaceutical formulations include compounds discovered by the screening method of the present invention.

Accordingly, the present invention is directed to a method for selecting compounds for use in treating sickle cell disease in a patient, comprising the steps of (a) selecting a first set of HbS ligands from a first group of chemical compounds; (b) selecting from said first set of HbS ligands a second set of HbS ligands that each exhibit inhibition of HbS polymerization; and (c) selecting from the second set of HbS ligands a third set of HbS ligands that each display anti-sickling activity.

It is contemplated that the steps (a) and (b) are repeated on analogs of a compound selected from the second set of HbS ligands. Further iterative cycles of screening and analog selection are contemplated.

The step of selecting a first set of HbS ligands may be accomplished by selecting those compounds which rate at least a specified measure of percent protease protection as determined by a methemoglobin S proteolysis assay of the first group of chemical compounds. It is preferred that the selected measure is approximately 3 standard deviations above the mean percent protease protection of a validation set of compounds randomly selected from the first group of chemical compounds. It is further preferred to exclude from the first set of HbS ligands those compounds that do not reproduce the assay results in a second methemoglobin S proteolysis assay, those compounds that cause aggregation, those compounds that inhibit protease proteinase K, and those compounds that contain moieties that bind to heme.

The step of selecting a second set of HbS ligands may be accomplished by selecting those compounds that rate at least a specified measure of gelation inhibition activity of deoxy-HbS. The specified measure of gelation inhibition activity is preferably at least 5 times the activity of tryptophan, measured as the increase in soluble deoxy-HbS per mM of tryptophan.

The effect on the $O_2$ affinity of HbS of a compound selected from the second set of HbS ligands may be determined by measuring the partial pressure of $O_2$ at which HbS is 50% saturated with bound $O_2$ in the presence of the compound. The anti-sickling activity of red blood cells may be determined by an assessment of red blood cell morphology in the presence and absence of a compound selected from the second set of HbS ligands. The cytotoxic effects to cell activity of a compound selected from the second set of HbS ligands may be determined using a microculture tetrazolium assay, wherein cell growth and viability in the presence and absence of a compound selected from the second set of HbS ligands may be assessed colorimetrically.

According to the present invention, a compound in the first set of HbS ligands may include an isoquinolium nucleus.

The present invention further contemplates a method for treating sickle cell disease in a patient, comprising administering to the patient a pharmaceutical formulation including an HbS ligand selected by the above-described method.

The present invention is additionally directed to a pharmaceutical formulation comprising a selected concentration of an HbS ligand and a pharmaceutically acceptable carrier therefor. In particular, the HbS ligand may be a quaternary ammonium salt, and specifically an isoquinolium derivative.

Isoquinolium derivatives of several general, as well as numerous specific, formulas are contemplated.

These and other objects of the present invention will become more readily appreciated and understood from a consideration of the following detailed description of the exemplary embodiment of the present invention when taken together with the accompanying drawings, in which:

DETAILED DESCRIPTION OF THE INVENTION

A very general separation-free technique for analysis of binding is the measurement of ligand-induced protein stabilization. This phenomenon is predicted on the basis of simple thermodynamic considerations and has been well characterized and thoroughly and quantitatively described. Pace et al., 255 J. Biol. Chem. 3862–65 (1980). This approach is applicable, in principle, to any folded protein target and to ligands of any chemical class that bind preferentially to the folded state of the target. Applicants have adapted this approach for high throughput discovery of novel ligands using resistance to proteolysis as a measure of protein folding. Here, Applicants describe the application of this high throughput screening technology, known as ATLAS (Any Target Ligand Affinity Screen), to the discovery of potential anti-sickling agents for use in the treatment of sickle cell disease. For a discussion of ATLAS, see U.S. Pat. Nos. 5,585,277 and 5,679,582 to Bowie et al., incorporated herein by reference. This approach allows the rapid prescreening by affinity of a large diverse population of molecules to identify HbS ligands, an attractive alternative to the prior art starting point in finding ligands that inhibit gelation of HbS.

The present invention provides a rapid and general means for identifying potential therapeutic agents directed at specific macromolecular targets central to sickle cell disease states. This approach operates on the principle that ligands stabilize protein structure upon binding. Structure stabilization can then be measured by resistance to protease digestion.

Applicants have developed a strategy to identify rapidly a relatively small number of sickle hemoglobin (HbS) ligands from a diverse library of thousands of small organic molecules. A high throughput assay was employed to identify small organic molecules that bind to and stabilize HbS. Subsequent testing for biochemical activity revealed several ligands that inhibit HbS polymerization, the underlying mechanistic cause of sickle cell disease. However, all of these exhibited low solubility, potentially limiting their potency and hampering further functional assessment.

Hence, analogs of these biochemically active ligands with enhanced solubility were sought by conducting substructure searches of the active ligands in large commercially available compound libraries. Those analogs found were then reevaluated by screening using ATLAS.

Iterations of this strategy incorporating the affinity-based screening approach of ATLAS technology followed by low throughput functional assays and analog searches yielded a series of quaternary ammonium salts that are both more soluble and more potent HbS polymerization inhibitors than the first set of active ligands. Several members of this series show significant anti-sickling activity, wherein sickling of intact erythrocytes is inhibited, making them good potential lead candidates in therapeutic drug discovery.

A. Materials

1. Hemoglobin S

Hemoglobin S from two sources was used. The initial 45,000 compound high through-put screen, discussed below, was conducted using lyophilized hemoglobin S (HbS) (Sigma Chemical). All subsequent work was done with HbS prepared from venous blood obtained, with informed consent, from homozygous sickle cell patients and anticoagulated with EDTA. The presence of sickle hemoglobin (SS) and not SA or SC types was confirmed by electrophoresis using Titan III cellulose acetate plates and $AFSA_2$ hemoglobin as a control (Helena Laboratories, TX). The total HbF content was determined to be less than 5%. Membrane free HbS was prepared using previously described modifications to the method of Rossi-Fanelli et al. De Croos et al., 33 J. Med Chem. 3138–42 (1990); Rossi-Fanelli et al., 270 J. Biol. Chem 391–96 (1961).

PK (Boehringer Mannheim) was used as received to prepare stock solutions in tris buffered saline (TBS) buffer at 10 mg/mL which were stored as small frozen aliquots at −20° C. until needed. Unused thawed enzyme was not reused.

2. Preparation of MetHbS

When using Sigma lyophilized HbS, the protein was first reduced by sodium dithionite (Aldrich Chemical) which was subsequently removed by gel filtration as follows. All water or buffers used for solutions and chromatography were $N_2$ spurged to remove $O_2$. One hundred milligrams of lyophilized HbS were dissolved in 2 mL of TBS, 10 mM tris pH 7.5, 150 mM NaCl, and transferred using a Hamilton gas tight syringe to a serum capped brown vial previously flushed with $N_2$. To the HbS solution 10 μL of a solution of sodium dithionite (1 M) in distilled water was added by syringe and gently stirred for 1 h to obtain reduced HbS (rHbS). Under a blanket of $N_2$. the protein was loaded onto a 50 mL, 30 cm long, column packed with G-25 Sephadex preequilibrated with TBS and eluted with the same buffer to remove reacted and excess sodium dithionite. The eluted HbS was concentrated by centrifugation in a Centriprep 10 tube (Amicon, Inc.) for at least 20 minutes at 3,000 rpms. The eluted HbS was adjusted to 2 mL by the addition of $N_2$ spurged TBS to achieve a 50 mg/mL HbS concentration divided into aliquots; and stored at −20 C. Oxidation to MetHbS was done in the ATLAS reaction mixture (see below) by inclusion of $K_3Fe(CN)_6$ (Sigma).

HbS, freshly prepared then immediately stored frozen in solution at −80° C. as HbSCO, was also used in ATLAS screening. In this case, CO was photodissociated in order to oxidize the ferrous iron of HbSCO to the ferric, or met, form in the presence of $K_3Fe(CN)_6$. ATLAS mixture was prepared as described above, using HbSCO instead of lyophilized HbS, and was gently stirred at 0° C. under a 75 Watt light bulb for 20 minutes. Oxidation was complete in 20 minutes as determined spectroscopically by monitoring the hemoglobin absorbance at 540 nm as a function of time.

B. Unfolding of Methemoglobin S

To establish that proteolysis would be a valid and useful measure of HbS unfolding, we examined proteolysis as a function of temperature. In the presence of oxygen, hemoglobin is readily converted to the met-hemoglobin form by oxidation of the porphyrin iron from the ferrous to the ferric state. Therefore, we chose to work with methemoglobin S (metHbS) to avoid this complication. In addition, the lower stability of methemoglobin permits thermal denaturation to be performed at more moderate temperatures. Lapshina et al., 26 Mol. Biol. (Mosk) 315–20 (1992).

Individual aliquots of metHbS were incubated with the nonspecific protease proteinase K ("PK") for 30 minutes at temperatures ranging from 0 to 67° C. Digestion was stopped by the addition of the protease inhibitor phenylmethylsulfonylfluoride ("PMSF"). Undigested protein was measured colorimetrically using a direct ELISA format or by dye binding using the Bradford reagent. Bradford, 22 Analytical Biochemistry 248 (1976).

Figure 1A:
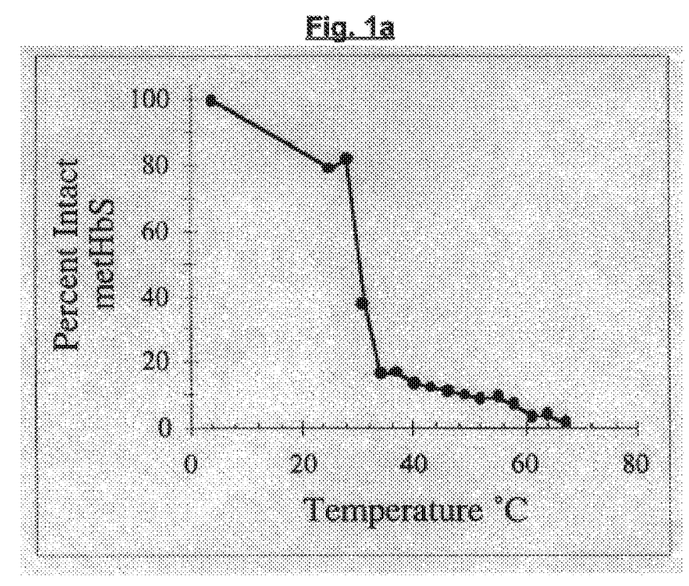
FIG. 1a depicts a plot of residual intact HbS protein after digestion with PK, as a function of temperature.

With reference to FIG. 1a, a plot of the residual intact protein as a function of temperature shows a sigmoidal curve characteristic of a cooperative unfolding event. The data for FIG. 1a was obtained by digesting individual aliquots of HbS with PK in a 6.9:1 ratio for 30 minutes at temperatures ranging from 4 to 67° C. Intact residual protein was measured using the Bradford reagent and is plotted as the percentage of protein remaining for digestion done at 4° C.

Thermolysin was also used yielding similar results (data not shown). PK was chosen for further work as it unfolded HbS at somewhat lower temperatures than did thermolysin.

Addition of azide, a ligand that binds to the iron atom of metHbA, was shown to thermally stabilize that protein. Klapper et al., 246 J. Biol. Chem. 6849–54 (1971); Cho et al., 622 Biochemica et Biophysica Acta 320 (1980). As azide also binds to metHbS, it was expected to stabilize this variant hemoglobin in a similar fashion. Rein et al., 94 Biochemica et Biophysica Acta 516–24 (1965).

Figure 1B:
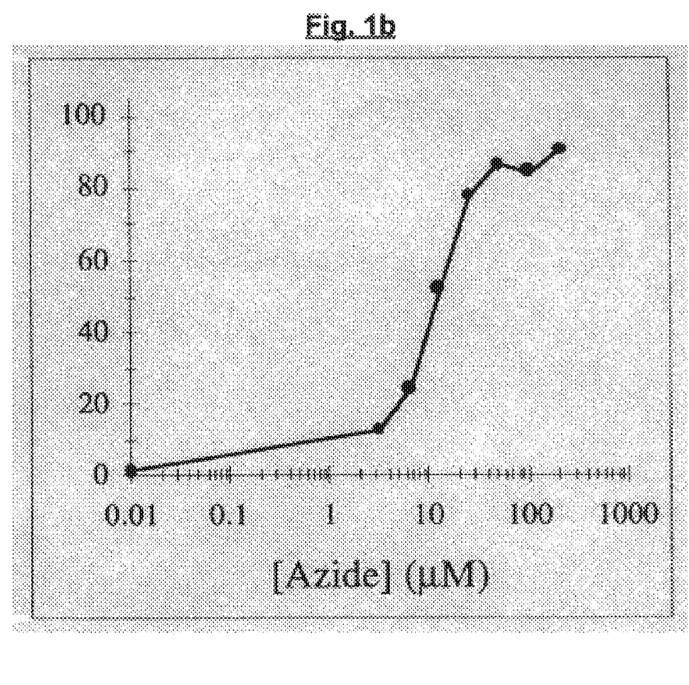
FIG. 1b depicts a plot of residual intact HbS protein after digestion with PK at 32° C. in the presence of sodium azide, as a function of sodium azide concentration.

With reference to FIG. 1b, a titration of azide demonstrates this stabilization by exhibiting increasing protection of HbS from proteolysis with increasing concentration of azide. The data for FIG. 1b was obtained from a protease digestion reaction of metHbS performed at 32° C. in the presence of increasing concentrations of sodium azide. Ligand stabilization is also evidenced in the cooperative thermal unfolding as monitored by circular dichroism at 220 nm; the unfolding curve dramatically shifts toward higher temperature upon addition of the known iron ligand potassium cyanide (data not shown).

The stabilization of MetHbS by $NaN_3$ was optimal at the midpoint temperature of 32° C. and was determined by performing azide titrations at two degree intervals between 28 and 34° C. At the midpoint temperature, the concentration at which azide inhibited proteolysis by 50%, IC50, is ~10 $\mu$M, a value close to the published $K_d$ of 50 $\mu$M measured under somewhat different solution conditions. Beetlestone, J. Chem. Soc. (Dalton) 1255–57 (1976). Potassium cyanide showed a similar titration curve (data not shown). Sodium azide was used as a positive control for the assay at its IC50.

C. Initial ATLAS screening and discovery of HbS ligands

A high throughput screen was developed by adapting the proteolysis assay to a 96 well plate format. For high throughput affinity screening of HbS, a protease ATLAS assay was first configured using PK as the protease. Colorimetric detection of undigested HbS was done using the Bradford reagent (Biorad). Bradford, 22 Analytical Biochemistry 248 (1976). The linear range for HbS detection was determined by titration to be 0–3.5 $\mu$g HbS. A 50 mL ATLAS reaction mixture was made by adding to 43 $\mu$L of a HbS solution composed of 0.32 mg/mL HbS, 0.4 mM $K_3Fe(CN)_6$, in TSG (50 mM Tris pH 7.6, 50 mM NaCl, 5% glycerol) 5 $\mu$L of DMSO and 2 $\mu$L of a 1 mg/mL PK solution yielding a HbS:PK mass ratio of 8:1. (The volume of ATLAS mixture for this and high throughput screening mode was scaled as needed.) Sixty $\mu$L aliquots were incubated in eppendorf tubes for 30 minutes at temperatures ranging from 4 to 48° C. Digestion is stopped by cooling on ice and adding 150 $\mu$L of stop buffer, 50 mM borate pH 8.5, 10 mM EDTA, plus 5 $\mu$L of 40 mM PMSF (Sigma) dissolved in ethanol. Samples were transferred to the wells of a 96 well polystyrene plate (Costar). To each well was added 160 $\mu$L of Bradford reagent, diluted 4:1 in water, and the plates were mixed in a 96 well plate mixer and read at 595 nm. A no-HbS blank is subtracted before plotting.

High throuphput ATLAS screening and secondary titrations are conducted in a similar fashion with all sample processing in the 96 well plate format.

Figure 2:
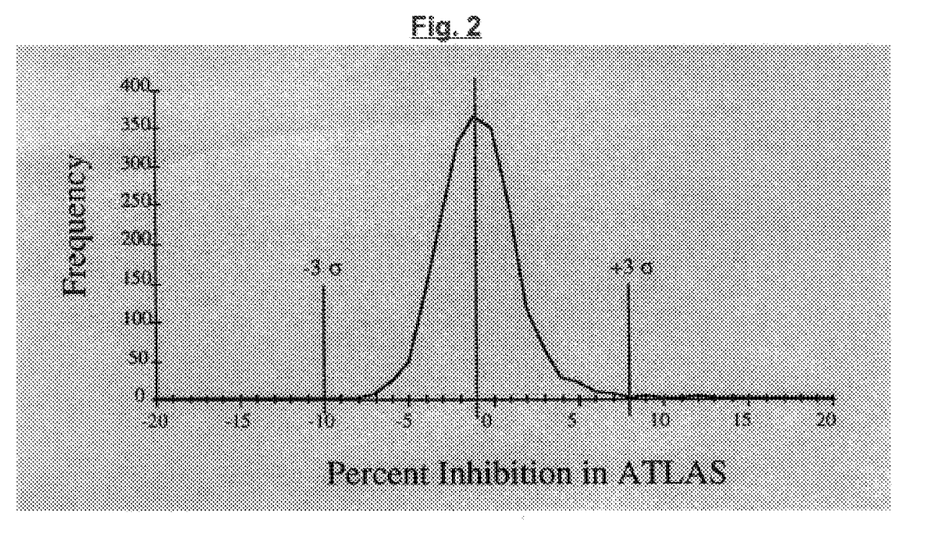
FIG. 2 depicts an ATLAS validation screening of 2001 compounds for percent protease protection.

An initial validation screening was performed with 2001 randomly selected, small molecules, to establish practical criteria for identifying ligands or positive hits. With reference to FIG. 2, a frequency plot of the percent protease protection for compounds was normally distributed about a mean of −1% protection with a standard deviation, $\sigma$, of ca. 3%. Percent protection is calculated from the optical density difference observed for protease digestion with compound present minus that observed without compound, both at 32° C., divided by the difference in optical density for digestion at 4° C. minus that for 32° C., both in the absence of compound.

A total of 45,000 small organic compounds were screened in high throughput. Compounds were counted positive if they scored +3$\sigma$ above the mean. This criterion yielded 357 (~0.8% of the compounds screened) positive hits including both ligands and false positives. False positives include those that: do not reproduce in ATLAS; cause aggregation, protecting the protein from protease digestion; inhibit PK; and/or contain moieties that bind to heme, thereby stabilizing the molecular structure against protease digestion. The latter were deemed undesirable as they would likely interfere with $O_2$ binding. A series of secondary screens were performed to eliminate false positives.

1. Verification of initial results

To verify the initial results, the ATLAS assay was either repeated at the single initial concentration or a titration was performed. For the latter, typical sigmoidal-shaped titration curves were observed as seen for the positive control, azide (FIG. 1b). Compounds could not always be titrated to 100% protection. While the reasons for this are not well understood it is suspected that limited solubility of some of the ligands at the higher concentrations may interfere with the assay. Of the 357 compounds testing positive 259 repeated or titrated in ATLAS. These were then tested for aggregation.

2. Aggregation

HbS aggregation was assessed by filtration of the protein after incubation with a given test compound. For each compound tested 100 $\mu$L of HbS ATLAS mix without PK and 10 $\mu$L of a 200 $\mu$M DMSO compound solution were mixed in a well of a 96 well polystyrene plate. HbS was incubated in the presence of compound at 32° C. for 30 minutes after which the absorbance was read at 570 nm. The sample was then transferred to the well of a 0.22 $\mu$ PVDF filter plate (Millipore Corp.) and filtered by vacuum into a second polystyrene plate. The absorbance was reread at 570 nm.

Aggregated HbS was filtered out of suspension, and the amount of HbS remaining in solution, i.e., not aggregated, determined spectroscopically. By using a no-compound reference as control, percent HbS aggregation was calculated from the difference in absorbance before and after filtration. Of the total, 62 caused aggregation and 197 (~0.4% OAS) did not.

3. Protease inhibition

To further eliminate compounds that primarily exhibit protease inhibition, all positives were tested at the screening concentration of ca. 6 mg/mL in a PK activity assay by colorimetrically measuring the rate of cleavage of the soluble calorimetric substrate N-Succinyl-Ala-Ala-Ala p-Nitroanilide ($NSA_3pN$) either in the absence or presence of test compound. The known serine protease inhibitor, phenylmethylsulfonylfluoride (PMSF), was titrated in both the ATLAS assay and PK enzymatic assays. Test compounds of PMSF were dissolved in dimethylsulfoxide (DMSO) at 200 µM. Stocks of 2 mM NSA₃pN in TBS were prepared fresh for each kinetic run and used promptly. Assays were performed in 96 well polystyrene plates. Runs were initiated by the addition of 50 µL of substrate to 50 µL of a solution of 0.1925 µM PK and 20 µM test compound in TBS with a final concentration of 11% DMSO. The reaction was followed by reading the absorbance at 405 nm every 15 seconds for 20 minutes in a Biorad model 3550-UV microplate reader. Percent inhibition was calculated from the ratio of the slopes of test compound to that of the no compound control.

A plot of the percent inhibition of PMSF in ATLAS against that in the PK assay yielded a straight line with a slope of about I (data not shown). All compounds falling on or above this line, i.e., exhibiting a larger percent inhibition in ATLAS than in the PK activity assay were counted as true ligands. The decision to include compounds that fall on the line was chosen to err on the side of retaining potential false positives rather than lose true ligands.

4. Results

Of the 197 compounds remaining after the aggregation assay, 166 were primarily protease inhibitors and 31 (~0.07% of the original compounds screened) were considered true ligands of HbS. Visible spectra of HbS in the presence of these ligands showed that two ligands perturbed the heme spectrum indicating that they, or associated impurities, bound within the heme pocket. These were no longer considered and the remaining 29 were tested for activity in inhibiting gelation.

D. Inhibition of gelation activity: the first line functional assay

True HbS ligands were evaluated for relevant biochemical activity by determining whether they could inhibit the polymerization of deoxy-HbS in vitro. Such determinations were made by preparing ca. 35% solutions of deoxy-HbS in the absence and presence of test ligand. Tryptophan ("Trp"), a known gelation inhibitor, was tested in parallel at single concentrations of 10 or 20 mM. Noguchi et al., 17 Biochemistry 5455–59 (1978). The solutions are centrifuged at high speed to separate polymerized gel from soluble protein. The concentration of the latter, or $C_{sat}$, was then determined spectroscopically. Initially, one point determinations were done as a functional screen. Activity is quantified as an increase in $C_{sat}$ per mM of test ligand. Compounds active in the single point screen were followed by $C_{sat}$ determinations at three ligand concentrations in the 0.1 to 2 mM range. For multiple point determinations, activity is the slope of a linear regression done on a plot of $C_{sat}$ versus ligand concentration. All activities are also expressed as ratios to the Trp reference.

Of the 29 ligands tested, five were active in this assay. One was zinc bacitracin and was not pursued further. The remaining compounds I, II, III, and IV in Table 1, below, inhibited gelation with activities ranging from 5 to 10 times that of tryptophan. The apparent activities shown, however, underestimate compound potency as a result of the limited solubilities of those compounds. In order to ensure maximum saturation of binding sites, HbS was equilibrated overnight in the oxygenated form with test compounds, before dithionite was added to produce deoxy-HbS.

Because low compound solubility did not permit true assessment of gelation inhibition and discouraged any serious consideration of those compounds as potential therapeutic lead candidates, where intraerythrocyte concentrations in excess of 500 µM might be desirable, substructures derived from the four compounds were designated and used to search for analogs with increased solubility and potency as gelation inhibitors. Sunshine et al., 275 Nature 238–40 (1978).

TABLE 1

Anti-gelation activity of four HbS ligands found from the initial ATLAS screening of 45,000 compounds.

| Ligand | | $C_{sat}$ Activity[§] Slope (g dL⁻¹ mM⁻¹) | R |
|---|---|---|---|
| I | (structure) | 1.4 ± 0.2 | 10.5 |
| II | (structure) | 0.8 ± 0.1 | 10.0 |
| III | (structure) | 1.0 | 8.5 |
| IV | (structure) | 0.6 | 4.8 |

[§]Activity inhibiting gelation is given both as the slope of the compound dose response, equal to the increase in grams of soluble HbS per mM concentration of compound from $C_{sat}$ measurements, and as R, the ratio of this slope to that for Trp.

Inhibition of deoxy-HbS polymerization was determined by methods previously described with modifications outlined by De Croos et al. Mazhani et al., Hemoglobin 129–136 (1984); De Croos et al., 33 J. Med. Chem. 3138–42 (1990). Typically compound, buffer blank, or Trp was added to fully oxygenated hemoglobin ($HbO_2$) in serum capped tubes, mixed by inversion, and equilibrated on ice for 10 minutes. $HbO_2$ was then reduced by addition of cold, $N_2$ purged, sodium dithionite solution buffered at pH 8.5 phosphate buffer. The final concentration of $HbO_2$ was 25 g/dL, Trp was 10 or 20 mM and compound varied. The mixture was incubated at 30° C. before separation of gelled deoxy-HbS from soluble protein. For the compounds in Table 1, which exhibited precipitate at the concentrations tested, 0.1 to 2.5 mM, incubation with cold HbO$_2$ was done overnight in an attempt to maximize the amount of compound bound to the protein before initiating deoxy-HbS polymerization at 30 C.

E. The search for better gelation inhibitors: analog by catalog

The search for analogs of I, II, III and IV led to a class of molecules that exhibit both increased solubility and gelation inhibition potency. The analog searching strategy proceeded as follows. Substructures of each of the four lead ligands from the initial screen were searched by computer in commercial compound libraries for structural analogs. In all, 517 analogs were procured and rescreened in ATLAS. Of these, 157 (30%) were hits; 4 were true positives having repeated in ATLAS, passed all the criteria set by the other secondary assays described above, and exhibited significant inhibition of HbS polymerization in C$_{sat}$ assays, i.e., up to 8-fold times Trp. Three of these displayed poor solubility, typically <30 μM, in aqueous solution and were not pursued further. However, one, V (first entry Table 2, below), a quaternary ammonium salt, displayed higher solubility but weak antigelation activity, i.e., 4-fold times Trp. Further efforts were focused on finding analog salts with greater potency.

A second substructure search of V was conducted to find analogs with greater potency. Of the 117 analogs found and screened in ATLAS, 63 (54%) tested positive and 20 (17%) were chosen after testing in secondary assays for C$_{sat}$ assays. Out of the 20, 3 showed no activity and 2 exhibited activity <9-fold times that of Trp; the remaining 15 inhibited HbS polymerization at levels ranging from 9–33-fold times that of Trp and the structure shown is consistent with the molecular weight obtained by mass spectroscopy. See Table 2, below. All but one have in common an isoquinolium nucleus, the exception being XI. Some of these salts were available in quantities that permitted further functional evaluation.

TABLE 2

Anti-gelation activity, oxygen binding affinity and anti-sickling activity for a series of small organic HbS ligands.

| Ligand | C$_{sat}$ Activity[§] | | Oxygen Affinity | Anti-sickling activity[⊥] |
| --- | --- | --- | --- | --- |
| | Slope (g dL$^{-1}$mM$^{-1}$) | R | pO$_2$ (50%)* (mm Hg) | % @ [Cpd] (mM) |
| V | 0.4 | 4 | ND | ND |
| VI | 1.9 | 33 | ND | ND |
| VII | 2.5 | 25 | ND | ND |

TABLE 2-continued

Anti-gelation activity, oxygen binding affinity and anti-sickling activity for a series of small organic HbS ligands.

| Ligand | $C_{sat}$ Activity[§] Slope (g dL$^{-1}$mM$^{-1}$) | R | Oxygen Affinity pO$_2$ (50%)* (mm Hg) | Anti-sickling activity[⊥] % @ [Cpd] (mM) |
|---|---|---|---|---|
| VIII | 2.0 | 25 | ND | −6 @ 2.5[pp] |
| IX | 2.4 ± 0.3[¶] | 24 | 10 | −1 @ 1.2 |
| X | 2.2 ± 0.3[¶] | 22 | 9.6 | 39 @ 1.0 |
| XI | 2.1 ± 0.2[¶] | 21 | 9.6 | 12 @ 2.6[pp] |
| XII | 2.0 ± 0.1[¶] | 20 | 10 | ND |

TABLE 2-continued

Anti-gelation activity, oxygen binding affinity and anti-sickling activity
for a series of small organic HbS ligands.

| Ligand | | $C_{sat}$ Activity[§] | | Oxygen Affinity | Anti-sickling activity[⊥] |
|---|---|---|---|---|---|
| | | Slope (g dL$^{-1}$mM$^{-1}$) | R | pO$_2$ (50%)* (mm Hg) | % @ [Cpd] (mM) |
| XIII | [structure] | 1.8 | 20 | ND | ND |
| XIV | [structure] | 1.4 ± 0.2[¶] | 18 | 10 | 67 @ 1.05[pp] |
| XV | [structure] | 1.6 ± 0.2[¶] | 15.7 | 9.7 | 41 @ 0.43[pp] |
| XVI | [structure] | 1.1 ± 0.2[¶] | 11 | 9.7 | −5 @ 1.05[pp] |
| XVII | [structure] | 2.0 | 10.5 | ND | ND |

TABLE 2-continued

Anti-gelation activity, oxygen binding affinity and anti-sickling activity for a series of small organic HbS ligands.

| | | $C_{sat}$ Activity[§] | | Oxygen Affinity | Anti-sickling activity[⊥] |
|---|---|---|---|---|---|
| Ligand | | Slope (g dL$^{-1}$mM$^{-1}$) | R | pO$_2$ (50%)* (mm Hg) | % @ [Cpd] (mM) |
| XVIII | (structure: 5-hydroxyisoquinolinium N-ethyl, Br$^-$) | 1.0 ± 0.1[¶] | 9.5 | 9.9 | 38 @ 1.06 |
| XIX | (structure: 6-hydroxy-7-methoxy-1-(3,4-dimethoxybenzyl)-2-methylisoquinolinium, Cl$^-$) | 1.8 | 9.6 | ND | ND |

[§]Activity inhibiting gelation is given both as the slope of the compound dose response, equal to the increase in grams of soluble HbS per mM concentraion of compound from $C_{sat}$ measurements, and as R, the ratio of this slope to that for Trp.
[¶]These slopes derive from $C_{sat}$ measurements at four different compound concentrations including zero. The slope is best fit from a linear regression of the data. All other gelation data is derived from a two point determination including the zero concentration.
*Partial pressure of O$_2$ at which HbS is 50% saturated in bound O$_2$. An equimolar Hb:compound ratio was used, with both at 4.34 mM.
[⊥]Anti-sickling activity is expressed as the difference between the percentage of cells that sickle and otherwise deform in the absense of compound minus the percentage that do so at the single mM compouind concentration ([Cpd]) sited. Four determinations of sickling for control cells show a range of values from 89 to 95%. The error in the measurement is taken as half this range, ±3%.
[PP]Precipitates at the concentration used.
ND Not determined.

F. Additional Functional Assays: O$_2$ binding, anti-sickling activity, and toxicity Compounds showing high activity in Csat assays were further tested to evaluate their effects on O$_2$ binding to HbS and sickling of intact SCD erythrocytes and to assess cytotoxicity.

1. O$_2$ Affinity Measurements

O$_2$ affinity measurements were conducted to determine whether the ligands perturb the O$_2$ binding curve of HbS. The pO$_2$(50), or partial pressure of O$_2$ at which HbS is 50% saturated with bound O$_2$, was determined for compounds exhibiting significant inhibition of gelation. Oxygen equilibrium measurements were obtained using a Hem-ox Analyzer (Technical Consulting Services). All determinations were done at 37° C. with HbS initially fully oxygenated at concentrations of 12%–14% in 50 mM pH 7.4 phosphate buffer.

Of the compounds tested, all showed a pO$_2$(50) of ca. 10 mm Hg, the same as that for the control. See Table 2. Therefore, it was concluded that these ligands do not affect O$_2$ affinity. It should be noted that $C_{sat}$ assays are typically done under anaerobic conditions. Therefore, the inhibition observed in this assay is independent of changes in O$_2$ affinity.

2. Anti-Sickling assays

Anti-sickling assays of intact erythrocytes were performed with eight of the gelation inhibitors. The assay consists of a visual assessment of red blood cell (RBC) morphology providing a measure of how this changes upon deoxygenation in the presence or absence of compound. The protocol is based on the general method of Bookchin et al., 87 J. Lab. Clin. Med. 597–616 (1976). The RBCs were washed three times with buffer A (in mM: 145 NaCl, 5 KCl, 10 Na-HEPES buffer pH 7.35, and 0.2 MgCl$_2$) and were suspended at 5% hematocrit in solution A containing 1 g/dL of human serum albumin. To 1 mL of RBC suspension 10 μL or less of DMSO with or without a test compound was added. The suspension was equilibrated in a tonometer (Model 237, Instrumentation Laboratory Inc., Lexington, Mass.) at 37° C. with water-saturated O$_2$ gas for about 5 min and then sampled: 50 μL of RBC suspension were mixed with 1 mL of 10% formalin in isotonic phosphate-buffered saline, pH 7.35. The remaining RBCs were then equilibrated with N$_2$ gas for 20 to 30 min and sampled again. In some experiments, the effects of partial deoxygenation was tested by substituting an O$_2$/N$_2$ gas mixture containing 4.2% O$_2$.

The RBC morphology was subsequently observed with a Zeiss Axiomatic microscope using Nomarsky optics. At least 400 cells were counted and tallied into four different categories identified on the basis of morphology and behavior. The cells were classified and tallied thus: normal (biconcave discs), sickled (exhibiting pointed projections), deformed (otherwise distorted from normal), and irregular (RBC deform promptly upon addition of compound with oxygen present). Both sickled and deformed were clearly induced upon deoxygenation.

It should be noted that blood from sickle cell patients contains RBCs that are irreversibly misshapen, i.e., they do not assume normal morphology in the presence of O$_2$. These were not included in calculating the percentage of cells that newly sickle upon deoxygenation.

Test compounds were dissolved in DMSO at either saturation or at concentrations which would result in approximately 1–3 mM final concentration in the red cell suspensions with a maximum of 1%(vol) DMSO. Separate preliminary solubility tests showed that some of the compounds precipitated upon addition of their DMSO stock solutions to the aqueous suspension buffer at or below the concentrations used, as indicated in the legend to Table 2.

Figure 3:
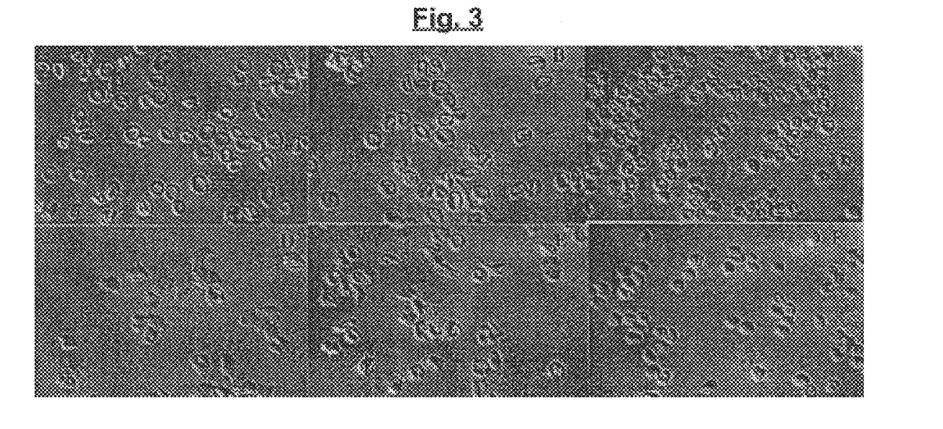
FIG. 3 depicts the inhibition of sickling activity in intact HbS erythrocytes.

With respect to FIG. 3, the effects of a compound on erythrocytes in the presence (A, B, C,) or absence (D, E, F) of oxygen were examined by fixing the cells in formalin after the appropriate incubation. Cells in A and D were not treated with compound. Cells in B and D were treated with compound X from Table 2. Cells in C and F were treated with compound XIV from Table 2. Compound concentrations used are in Table 2.

Sickling was quantitated by calculating the percentage of cells undergoing morphological changes upon deoxygenation. Anti-sickling activity is reported as this percentage in the absence of compound minus that in the presence of compound. Three of the compounds, X, XV and XVIII, protect about 40% of the cells from sickling while one, XIV, protects nearly 70% at the concentrations tested. See Table 2. A fifth, XI, shows weak anti-sickling activity at 12%. A sixth, IX, shows no activity and two, VIII and XVI exhibit small negative, or sickling, activity.

Most of the anti-sickling agents did not affect the morphology of oxygenated RBCs. The exceptions to this are XI and XIV (FIG. 3C) which induced abnormal morphology in 100% and 85% of the oxygenated cells, respectively. The most active of these, XIV, was examined more closely. When RBCs were treated with XIV and washed twice with buffer A the percentage of abnormal cells decreased to about 60% but the protective effect remained high at ca. 62%. The anti-sickling activity may be the result of a chemical activity other than noncovalent inhibition of gelation. For example, XIV is a succinimide and may react with membrane protein thiols. More detailed investigations of the cellular-level activity are in progress.

3. Cytotoxicity

Cytotoxicity of the active anti-sickling agents was assessed by measuring cellular activity using a microculture tetrazolium assay. Scudiero et al., 48 Cancer Research 4827–33 (1988). In particular, drug sensitivity was evaluated using the tetrazolium, XTT, based in vitro toxicology assay kit from Sigma. CV1 cells were plated into 96 well tissue culture plates at a density of $1 \times 10^5$ cells/mL, and allowed to grow for 12 hours at 37° C. in Delbecco's Modified Eagles Medium (DMEM) with 50 $\mu$g/mL gentamycin. Compounds dissolved in dimethylsulfoxide (DMSO) were added to the desired compound concentration with a final DMSO concentration of 1%. The cells were allowed to grow for 25 hours. After washing with PBS the cells were resuspended in DMEM containing XTT without phenol red or serum, allowed to incubate for 4 hours, and then read at 450 and 655 nm in a plate reader. The reading at 655 nm was used to subtract the effects of light scattering.

In this manner the combined effects of cell growth and viability were assessed colorimetrically by allowing CV1 cells to grow for one day in the absence or presence of compound and then measuring absorbance at 450 nm.

Three of the compounds, X, XIV and XVIII were tested at 0.25, 2.5, 25 and 250 $\mu$M and XV was tested at 0.1, 1, 10 and 100 $\mu$M. Compared to control cells, XVIII affected no change in cellular activity throughout the concentration range, and X affected ca. a 15% drop in cellular activity only at 250 $\mu$M. In the presence of XV, cells showed 80% of the activity of control cells at all concentrations, and with XIV cells exhibited 80% of their activity for all but the highest concentration, at which total activity dropped to about 50%.

From this it was concluded that none of the four compounds appear highly toxic in the concentration ranges examined. The most active anti-sickling agent, XIV, does affect cell activity at higher concentrations.

G. Summary of Results

Using ATLAS technology, a modest screen of ca. 45,000 structurally diverse compounds for HbS inhibitors successfully yielded 14 with activities that are 10-fold that seen for Tryptophan ("Trp") and several that are 20-fold or greater. It has been reported that Trp is approximately twice as potent a gelation inhibitor as phenylalanine ("Phe"). Poillon, 21 N. Biochemistry 1400–06 (1982). It has been suggested that a potency of 10 times that of Phe is sufficient to reduce the clinical symptomology of sickle cell anemia to that of the less severe form of SCD, S/$\beta^+$-thalasemia. Sunshine et al., 275 Nature 238– 40 (1978). Expressed in different terms, a compound must increase the solubility of deoxy-HbS by about 6–17% to affect milder symptomology.

Given the activities of the quaternary ammonium salts in Table 2, those with a slope of ~2.4 or greater could achieve this at concentrations of 0.7 mM or less, a nearly 7-fold increase in potency over most of those previously tested. In addition to being potent inhibitors of HbS polymerization, four of the inhibitors, X, XIV, XV, and XVIII, exhibit significant anti-sickling activity. See Table 2. None of these four inhibitors affects the $O_2$ binding properties of HbS. This is an important observation as a compound can affect inhibition of polymerization by shifting the HbS $O_2$ binding curve to lower partial $O_2$ pressure, i.e., induce tighter $O_2$ binding, without interfering with intermolecular deoxy-HbS interactions. Used as a therapeutic this molecule might create a blood that released less $O_2$ to the tissues, effectively negating, at least in part, any benefits afforded by decreased HbS polymerization.

In addition to biological potency, a good drug lead must also have a good pharmacokinetic profile exhibiting bioavailability, low toxicity and efficacy in animal models and ultimately, humans. Assessments of these properties are in progress.

The means to screen large libraries rapidly and conveniently provides advantages and flexibility in the design of discovery strategies. For example, in the case presented here, four molecules, I–IV, found from an initial HTS screen showed activity in inhibiting deoxy-HbS polymerization. However, low solubilities precluded a true assessment of their biochemical potency. Such low solubilities also gave little promise for their potential use as therapeutics. However, one round of screening analogs yielded the isoquinolium salt V (Table 2) with enhanced solubility but poor performance as a gelation inhibitor. A second round of screening analogs obtained by analoging the salt V were quickly screened to yield the more potent and more soluble entries of Table 2, VI–XIX.

By extension, if a lead anti-sickling candidate, like XIV, fails to satisfy any subsequent criterion along the discovery pathway, in addition to addressing these issues by the traditional synthetic methods of medicinal chemistry, a new (or larger) screening can be readily undertaken to search for analogs with improved properties or for completely different molecular classes that exhibit the desirable attributes. Another possible strategy might couple a combinatorial expansion around the isoquinolium nucleus and prescreening the analogs using ATLAS in search of isoquinolium derivatives that perform better. At the current screening rate of 5,000 compounds/day most libraries spanning isoquinolium space can be screened in less than a week.

Although it is preferable to have pure protein, the methodology works in configurations for less pure mixtures.

ELISA assays employing conformationally specific monoclonal or polyclonal antibodies, that recognize either the folded or unfolded protein, have been successfully used in ATLAS. For HbS, the Bradford reagent was chosen as the detection system because HbS is relatively abundant. When less protein is available, more sensitive ELISA-based assays can be used. In such cases typically 50 ng protein/compound is required. As an example, the identification of ligands from 250,000 compounds would require ~13 mg of target protein. Screening can be further accelerated by: employing more labor or more equipment in parallel activities; utilizing plates with higher well-density; and/or automating the screening with robotics. The latter two are currently being developed. Approximately an additional order of magnitude in speed is attainable.

It should be appreciated from the foregoing that the present invention contemplates the discovery of additional organic HbS ligands and their pharmaceutical formulations for use in treating sickle cell disease. These organic ligands may be quaternary ammonium salts, specifically isoquinolium derivatives, or other compounds discovered by the method of the present invention to be effective in treating sickle cell disease.

In particular, compounds of formulas I, II and III are contemplated:

Formula I

Formula II

Formula III wherein $R_{1-12}$ are organic radicals and wherein $X^-$ is an anion. In particular, it is contemplated that $R_1$ and $R_{3-12}$ are each chosen from a group consisting of hydrogen, halogen, hydroxy, nitro, cyano, aryl, alkyl, alkeneyl, alkynyl, trihalomethyl, carbonyl, amino, alkoxy, aryloxy, cycloalkyl, cycloalkeneyl, fused cycloalkyl, fused cycloalkeneyl, fused aryl, and fused heteroaryl; and $R_2$ is chosen from a group consisting of hydrogen, alkyl, alkeneyl, alkynyl, aryl, alkyl aryl, alkeneyl aryl, alkynyl aryl, alkyl alkoxy, alkeneyl alkoxy, alkynyl alkoxy, aryloxy, alkyl amino, alkeneyl amino, alkynyl amino, aryl amino, alkyl carbonyl, alkyl carbonyl aryl, alkeneyl carbonyl, alkynyl carbonyl, aryl carbonyl, alkyl ester, alkeneyl ester, alkynyl ester, aryl ester, alkyl amide, alkeneyl amide, alkynyl amide, aryl amide, alkyl carboxylic acid, imino, alkeneyl carboxylic acid, alkynyl carboxylic acid, aryl carboxylic acid, cyclo alkyl, and cyclo alkeneyl; and $X^-$ is a counterion chosen from a group consisting of halogen, mesylate, tosylate, $HSO_4$, and $SO_3CH_2COOH$.

More specifically, $R_{1-12}$ are selected from the group consisting of hydrogen, hydroxyl, methyl, ethyl, methoxy, and the following radicals:

and $R_6$ and $R_7$ may additionally form a heterocyclic ring containing oxygen, and $R_{10}$ and $R_{11}$ may additionally form a heterocyclic ring containing oxygen and X may be selected from the group consisting of I, Br, Cl, $HSO_4$, and $SO_3CH_2COOH$.

In particular, it is contemplated that $R_1$ is selected from the group consisting of hydrogen, methyl and the following radicals:

-continued $R_2$ is selected from the group consisting of hydrogen, methyl, ethyl and the following radicals:

$R_3$ is selected from the group consisting of hydrogen and methyl; $R_4$ is selected from the group consisting of hydrogen and $R_5$ is selected from the group consisting of hydrogen and hydroxyl; $R_6$ is selected from the group consisting of hydrogen, hydroxyl, methoxy and oxygen, and when $R_6$ is oxygen, $R_7$ is also oxygen and $R_6$ and $R_7$ are connected by a —$CH_2$— group to form a heterocyclic ring; $R_7$ is selected from the group consisting of hydrogen, methoxy and oxygen, and when $R_7$ is oxygen, $R_6$ is also oxygen and $R_6$ and $R_7$ are connected by a —$CH_2$— group to form a heterocyclic ring; $R_8$ is selected from the group consisting of hydrogen, hydroxyl, and methoxy; $R_9$ is hydrogen; $R_{10}$ is selected from the group consisting of methoxy and oxygen, and when $R_{10}$ is oxygen, $R_{11}$ is also oxygen and $R_{10}$ and $R_{11}$ are connected by a —$CH_2$— group to form a heterocyclic ring; $R_{11}$ is selected from the group consisting of hydroxyl, methoxy and oxygen, and when $R_{11}$ is oxygen, $R_{10}$ is also oxygen and $R_{10}$ and $R_{11}$ are connected by a —$CH_2$— group to form a heterocyclic ring; and $R_{12}$ is hydrogen.

The present invention also contemplates pharmaceutical formulations of the above compounds, as well as compounds V to XIX of Table 2 for use in the treatment of sickle cell disease. In addition, the present invention contemplates methods for treating sickle cell disease in a patient comprising administering to the patient pharmaceutical formulations including pharmaceutically effective amounts of one or more of the above contemplated HbS ligands, as well as additional HbS ligands discovered by the screening methods of the present invention.

It is further contemplated that any suitable route of administration may be employed for providing a patient with an effective dosage of a compound disclosed herein. For example, oral, rectal, topical, enteral, parenteral, ocular, pulmonary, nasal, etc., routes may be employed. Dosage forms include tablets, troches, dispersions, suspensions, solutions, capsules, creams, ointments, aerosols, etc.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. It should be appreciated that the most suitable route in any given case will depend largely on the nature and severity of the condition being treated and on the nature of the active ingredient. An active ingredient may be conveniently presented in unit dosage form and prepared by any of the methods well known in the art of pharmacy.

In preparing oral dosage forms, any of the usual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations, which are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

As used herein, the term "aryl" means an aromatic carbocyclic ring system having a single radical containing about 6 to about 10 carbon atoms. An aryl group may be a fused or polycyclic ring system. Exemplary aryl groups include phenyl or napthyl.

As used herein, the term "aryloxy" 'means an O-aryl group. An aryloxy group is optionally substituted on the aryl moiety of the aryloxy. Suitable substituents include halogen, hydroxy, alkyl, nitro, trihalomethyl, aryl, aryloxy, alkoxy, amino, carbonyl, carboxyl, ester, amide, primary, secondary or tertiary amines, cyano, cycloalkyl, alkenyl, cycloalkenyl and alkynyl.

As used herein, the term "alkyl" means a straight or branched saturated hydrocarbon group. Preferred alkyl groups include those having from 1–12 carbon atoms.

As used herein, the term "cycloalkyl" means a non-aromatic monocyclic or fused or polycyclic ring system of about 3 to about 10 ring carbon atoms. Optionally one or more of the ring carbon atoms of the cycloalkyl may be replaced by a heteroatom, such as nitrogen, oxygen or sulfur. Exemplary cycloalkyl groups include cyclohexyl.

As used herein, the term "cycloalkenyl" means a non-aromatic monocyclic or fused or polycyclic ring system containing a carbon-carbon double bond and having about 3 to about 10 ring carbon atoms. Optionally one or more of the ring carbon atoms of the cycloalkyl may be replaced by a heteroatom, such as nitrogen, oxygen or sulfur.

As used herein, the term "carbonyl" or "carbonyl moiety" refers to any chemical moiety comprising a carbonyl functional group, e.g., a ketone, aldehyde, carboxylic acid, acid halide, amide, peptide, anhydride and ester. As used herein, when a non-aromatic ring structure is described as substituted with a carbonyl group, the ring carbon atom is replaced by the >C=O group.

As used herein, the term "heteroatom" includes nitrogen, oxygen and sulfur, as well as any atom other than a carbon.

As used herein, the term "ring system" refers to an aromatic or non-aromatic carbocyclic compound, in which one or more of the ring carbon atoms may be replaced by a heteroatom, such as nitrogen, oxygen or sulfur. The ring system may be optionally substituted by one or more halogens, $C_1$ to $C_{12}$ alkyl, aryl, vinyl, alkyl(aryl), vinyl(aryl) and nitro groups.

As used herein, the term "fused ring system" refers to ring systems wherein at least two adjacent carbon centers join one or more cyclic structures. A fused ring system as used herein may be aromatic or non-aromatic, or may be composed of separate aromatic and non-aromatic moieties. Exemplary carbocyclic fused ring systems are represented by the formulas:

Exemplary fused ring systems in which one or more of the ring carbon atoms is replaced by a heteroatom include the following:

As used herein, the term "polycyclic ring system" refers to ring systems having two or more cyclic compounds bonded in tandem. A polycyclic ring system as used herein may be aromatic or non-aromatic, or may be composed of separate aromatic and non-aromatic moieties. An exemplary carbocyclic polycyclic ring system is represented by the formula:

An exemplary polycyclic ring system in which one or more of the ring carbon atoms is replaced by a heteroatom include the following:

Additionally, fused or polycyclic ring systems may optionally be substituted by one or more halogens, $C_1$ to $C_{12}$ alkyl, aryl, vinyl, alkyl(aryl), vinyl(aryl) and nitro groups.

As used herein, the term "heteroaryl" means an about 5 to 10-membered aromatic monocyclic or fused or polycyclic ring system having a single radical in which one or more of the carbon atoms in the ring system is other than carbon, for example, nitrogen, oxygen or sulfur. An exemplary heteroaryl group is pyridine. An exemplary fused or polycyclic heteroaryl group is indole.

As used herein, the term "heterocyclyl" or "heterocyclic" means an aromatic or non-aromatic about 5 to about 10-membered monocyclic or fused or polycyclic ring system in which one or more of the carbon atoms in the ring system is other than carbon, for example, nitrogen, oxygen or sulfur. A heterocyclyl group may be a fused or polycyclic ring system. Exemplary heterocyclyl groups include piperidine, morpholino, and azepanyl.

As used herein, the term "primary, secondary, or tertiary amine" refers to amine compounds having one, two, or three functional groups, respectively. Suitable functional groups include halogens, amines, $C_1$ to $C_{12}$ alkyl groups, aryl, vinyl, alkyl(aryl), vinyl(aryl) and nitro groups.

As used herein, the term "amide" refers to groups having the amide functional group —C(O)NH—, wherein alkyl, alkenyl or alkynyl groups may be bonded to the C or N atom of the amide group.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. A method for selecting compounds for use in treating sickle cell disease in a patient, comprising the steps of:
   (a) selecting a first set of HbS ligands from a first group of chemical compounds;
   (b) selecting from said first set of HbS ligands a second set of HbS ligands that each exhibit inhibition of HbS polymerization; and
   (c) selecting from the second set of HbS ligands a third set of HbS ligands that each display anti-sickling activity of red blood cells when in the presence thereof.

2. A method according to claim 1 including the step of preparing a pharmaceutical formulation containing a compound selected from the third set of HbS ligands.

3. A method according to claim 1 wherein steps (a) and (b) are repeated on analogs of a compound selected from the second set of HbS ligands.

4. A method according to claim 3 including the step of excluding from the analogs those compounds that display poor solubility in aqueous solution, prior to repeating steps (a) and (b).

5. A method according to claim 1 wherein steps (a) and (b) are repeated on compounds having a substructure common with a compound selected from the second set of HbS ligands.

6. A method according to claim 1 including the step of performing a methemoglobin S proteolysis assay measuring a percent protease protection for each compound in the first group of chemical compounds, and wherein the step of selecting a first set of HbS ligands is accomplished by selecting each compound in the first group of chemical compounds which rates at least a specified measure of percent protease protection.

7. A method according to claim 6 wherein said specified measure is approximately 3 standard deviations above a mean percent protease protection of a validation set of compounds randomly selected from said first group of chemical compounds.

8. A method according to claim 6 wherein said specified measure is approximately +8% protease protection.

9. A method according to claim 6 including the step of performing a methemoglobin S proteolysis assay measuring the percent protease protection of the first set of HbS ligands and eliminating from the first set of HbS ligands any compound not having at least the specified measure of percent protease protection.

10. A method according to claim 6 including the step of measuring HbS aggregation in the presence of compounds selected from the first set of HbS ligands and eliminating from the first set of HbS ligands those compounds that cause HbS aggregation.

11. A method according to claim 10 wherein the step of measuring HbS aggregation is accomplished by incubating HbS for a selected interval of time in the presence of a compound selected from the first set of HbS ligands and measuring the amount of HbS remaining in solution after the selected interval of time.

12. A method according to claim 6 including the step of measuring inhibition of protease of compounds selected from the first set of HbS ligands and eliminating from the first set of HbS ligands those compounds that inhibit protease.

13. A method according to claim 6 including the step of eliminating from the first set of HbS ligands those compounds that contain moieties that bind to heme.

14. A method according to claim 1 including the step of measuring deoxy-HbS gelation inhibition activity for each compound in the first set of HbS ligands, and wherein the step of selecting a second set of HbS ligands is accomplished by selecting each compound that rates at least a specified measure of gelation inhibition activity of deoxy-HbS.

15. A method according to claim 14 wherein the specified measure of gelation inhibition activity is at least 5 times the activity of tryptophan, measured as the increase in soluble deoxy-HbS per mM of tryptophan.

16. A method according to claim 1 wherein the anti-sickling activity of red blood cells is determined by an assessment of red blood cell morphology in the presence and absence of a compound selected from the second set of HbS ligands.

17. A method according to claim 1 including the step of inducing morphological changes of red blood cells by deoxygenation, and wherein the anti-sickling activity is determined by measuring the number of cells undergoing morphological changes in the presence and absence of a compound selected from the second set of HbS ligands.

18. A method according to claim 1 including the step of measuring the $O_2$ affinity of HbS in the presence of compounds selected from the third set of HbS ligands and eliminating from said third set of HbS ligands those compounds that adversely affect the $O_2$ affinity of HbS.

19. A method according to claim 18 wherein the effect on the $O_2$ affinity of HbS of a compound selected from the second set of HbS ligands is determined by measuring the partial pressure of $O_2$ at which HbS is 50% saturated with bound $O_2$ in the presence of the compound.

20. A method according to claim 1 including the step of measuring cytotoxic effect of compounds selected from the third set of HbS ligands and eliminating from said third set of HbS ligands those compounds that display a cytotoxic effect to cell activity at a selected concentration.

21. A method according to claim 20 wherein the cytotoxic effect to cell activity of a compound selected from the second set of HbS ligands is determined by performing a microculture tetrazolium assay.

22. A method according to claim 20 wherein the cytotoxic effect is measured by assessing colorimetrically cell growth and viability in the presence and absence of a compound selected from the second set of HbS ligands.

23. A method according to claim 1 wherein the first set of compounds includes compounds having an isoquinolium nucleus.

24. A method of treating sickle cell disease in a patient comprising administering to the patient a pharmaceutical formulation including a selected concentration of an HbS ligand and a pharmaceutically acceptable carrier therefor, wherein the HbS ligand exhibits inhibition of HbS polymerization and displays anti-sickling activity of red blood cells when in the presence thereof.

25. A method according to claim 24 wherein said HbS ligand does not adversely affect the $O_2$ affinity of HbS.

26. A method according to claim 24 wherein said HbS ligand displays a sufficiently minimal cytotoxic effect to cell activity at the selected concentration.

27. A method according to claim 24 wherein said HbS ligand is an isoquinolium derivative.

28. A method according to claim 24 wherein said HbS ligand is selected from the group consisting of formulas V to XIX as follows:

Formula V

Formula VI

Formula VII

Formula VIII

Formula IX

Formula X

Formula XI

Formula XII

Formula XIII

Formula XIV

Formula XV

Formula XVI

-continued

Formula XVII

Formula XVIII

-continued

Formula XIX

* * * * *